(12) United States Patent
Omura et al.

US006747056B2

(10) Patent No.: US 6,747,056 B2
(45) Date of Patent: Jun. 8, 2004

(54) K99-5041 SUBSTANCE AND PRODUCTION THEREOF

(75) Inventors: Satoshi Omura, Tokyo (JP); Hiroshi Tomoda, Tokyo (JP); Yoko Takahashi, Tokyo (JP); Yutaka Ebizuka, Kanagawa (JP); Masaaki Shibuya, Saitama (JP)

(73) Assignee: The Kitasato Institute, Tokyo (JP)

( * ) Notice: Subject to any disclaimer, the term of this patent is extended or adjusted under 35 U.S.C. 154(b) by 0 days.

(21) Appl. No.: 10/359,145

(22) Filed: Feb. 6, 2003

(65) Prior Publication Data

US 2004/0002533 A1 Jan. 1, 2004

(30) Foreign Application Priority Data

Mar. 20, 2002 (JP) ........................................ 2002-078019

(51) Int. Cl.$^7$ ..................... A61K 31/40; C07D 207/323; A61P 9/10
(52) U.S. Cl. ........................................ 514/438; 548/565
(58) Field of Search ........................... 514/438; 548/565

Primary Examiner—Joseph K. McKane
Assistant Examiner—Andrea D. Small
(74) Attorney, Agent, or Firm—Young & Thompson

(57) ABSTRACT

The present invention comprising culturing a microorganism which belongs to genus Streptomyces and has ability to produce K99-5041-C1x substance and/or K99-5041-C2x substance in a medium, accumulating K99-5041-C1x substance and/or K99-5041-C2x substance in the culture fluid, and isolating K99-5041-C1x substance and/or K99-5041-C2x substance form the cultured mass. Since the obtained K99-5041-C1x substance and/or K99-5041-C2x substance exhibit inhibitory activity against lanosterol synthase, these substances are expected to apply clinically for preventive and therapeutic agents caused by accumulation of cholesterol in humans and antifungal agents.

12 Claims, 8 Drawing Sheets

K99-5041 SUBSTANCE AND PRODUCTION THEREOF

TECHNICAL FIELD

The present invention relates to novel K99-5041 substance having inhibitory action for lipid metabolism and a process for production thereof.

BACKGROUND ART

Prior Art

Sterol such as cholesterol in human or ergosterol in fungi is biosynthesized. Enzymes involved in the sterol biosynthesis are recognized as the targets for development of preventive and therapeutic agents for human hyperlipidemia or arteriosclerosis and development of antifungal agents (Tomoda, H. and Omura, S.: Enzyme Technology for Pharmaceutical and Biological Applications, Ed. Kirst, A. et al., Chapter 15, pp. 343–378, Marcel Dekker, Inc. NY, 2001).

Statin series compounds represented by pravastatin specifically inhibit hydroxymethylglutaryl-coenzyme A (HMG-CoA) reductase, a one of rate-limiting enzyme of cholesterol biosynthesis, and reduce cholesterol level in blood, and are used as preventive and therapeutic drugs for arteriosclerosis in clinical practice. However, in case of statin series compounds used at present, there is a possibility to inhibit biosynthesis of non-sterol compounds which are essential components in vivo. Consequently, enzymes involved in the downstream from squalene which is an intermediate in the biosynthesis are expected as superior target for drugs.

Azole series compounds used for treatment of mycosis such as 2,4-difluoro-α,α-bis-(1H,1,2,4-triazole-1-ylmethyl)benzyl alcohol (generic name: fluconazole, I.C.N. Pharmaceuticals Inc., U.S.A.) and 1-[2-(2,4-dichlorobenzyloxy)-2-(2,4-dichlorophenyl)ethyl]imidazole (generic name: miconazole, Sigma Inc., U.S.A.) are used in practice as antifungal agents which inhibit C-14 demethylation of ergosterol. However, appearance of drug resistant microorganisms caused by long-term or repetitive administration of azole series antifungal agents becomes problem. Consequently, development of drugs with high safety and low incidence of resistant strains is urgently necessary.

Lanosterol synthase is an enzyme generating lanosterol by cyclization of 2,3-oxidosqualene as a substrate and drugs which inhibit such enzyme has not been utilized. Consequently, discovery of pharmaceutical agents which inhibit such the enzyme is thought to solve above problems and are expected to be used in clinical practice as preventive and therapeutic agents for myocardial infarction and cerebral apoplexy caused by hyperlipidemia and arteriosclerosis, or new antifungal agents.

An object of the present invention is to provide novel K99-5041 substance, which is used for clinical practice as preventive or therapeutic agents for diseases caused by accumulation of cholesterol in humans by inhibitory action against lanosterol synthase, and process for production thereof.

DISCLOSURE OF THE INVENTION

We have studied on metabolites produced by microorganisms, and found that substances having inhibitory activity for lanosterol synthase were produced in a culture mass of a microbial strain K99-5041 which was newly isolated from soil. Subsequently, we have isolated and purified the active substance inhibiting lanosterol synthase from the cultured mass, and found substances having chemical structure represented by the formula [I] and [II] hereinbelow. Since these substances have not been known, the substances are designated as K99-5041-C1x substance and K99-5041-C2x substance, and totally designated as K99-5041 substance.

The present invention has been completed based on the above knowledge. An object of the present invention is to provide K99-5041-C1x substance represented by the following formula [I]:

[I]

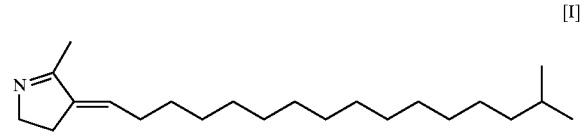

Another object of the present invention is to provide K99-5041-C2x substance represented by the following formula [II]:

[II]

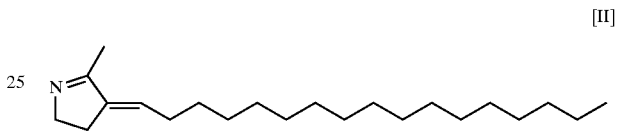

Further object of the present invention is to provide a composition of novel K99-5041 substance comprising especially K99-5041-C1x substance represented by the following formula [I]:

[I]

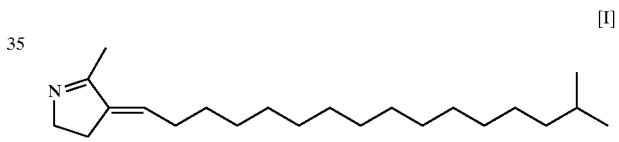

and especially K99-5041-C2x substance represented by the following formula [II]:

[II]

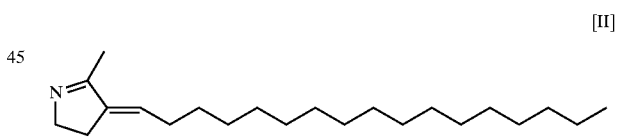

More further object of the present invention is to provide a process for production of K99-5041-C1x substance comprising culturing a microorganism belonging to genus Streptomyces and having ability to produce K99-5041-C1x substance in a medium, accumulating K99-5041-C1x substance in a culture fluid and isolating K99-5041-C1x substance from the cultured mass.

Still further object of the present invention is to provide a process for production of K99-5041-C2x substance comprising culturing a microorganism belonging to genus Streptomyces and having ability to produce K99-5041-C2x substance in a medium, accumulating K99-5041-C2x substance in a culture fluid and isolating K99-5041-C2x substance from the cultured mass.

Still more further object of the present invention is to provide a process for production of a composition of K99-5041 substance comprising culturing a microorganism belonging to genus Streptomyces having ability to produce K99-5041-C1x substance and/or K99-5041-C2x substance in a medium, accumulating K99-5041-C1x substance and/or K99-5041-C2x substance in a culture fluid and isolating K99-5041-C1x substance and/or K99-5041-C2x substance from the cultured mass.

Further object of the present invention is to provide a process for production of K99-5041-C1x substance and/or K99-5041-C2x substance wherein a microorganism belonging to genus Streptomyces and having ability to produce K99-5041-C1x substance and/or K99-5041-C2x substance is Streptomyces sp. K99-5041 FERM BP-8272.

Further object of the present invention is to provide a microorganism of Streptomyces sp. K99-5041 FERM BP-8272.

Further object of the present invention is to provide K99-5041-C1x substance, K99-5041-C2x substance or a composition of K99-5041-C1x substance and/or K99-5041-C2x substance for use as a medicament.

Further object of the present invention is to provide K99-5041-C1x substance, K99-5041-C2x substance or a composition of K99-5041-C1x substance and/or K99-5041-C2x substance used for inhibiting lanosterol synthase which synthesizes lanosterol generated by cyclization of 2,3-oxidosqualene as a substrate.

Further object of the present invention is to provide K99-5041-C1x substance, K99-5041-C2x substance or a composition of K99-5041-C1x substance and/or K99-5041-C2x substance used for preventing or treating diseases of myocardial infarction or cerebral apoplexy based on hyperlipidemia and arteriosclerosis caused by accumulation of cholesterol in humans.

Further object of the present invention is to provide K99-5041-C1x substance, K99-5041-C2x substance or a composition of K99-5041-C1x substance and/or K99-5041-C2x substance used for manufacture of drug preparations for inhibiting myocardial infarction, cerebral apoplexy or mycosis.

Further object of the present invention is to provide K99-5041-C1x substance, K99-5041-C2x substance or a composition of K99-5041-C1x substance and/or K99-5041-C2x substance used for prevention or treatment of diseases including myocardial infarction, cerebral apoplexy or mycosis.

The microorganism having ability to produce K99-5041-C1x substance represented by the above formula [I] and K99-5041-C2x substance represented by the above formula [II] or a composition thereof (hereinafter designates as "K99-5041 substance producing microorganism") belongs to genus Streptomyces, and, for example, a strain Streptomyces sp K99-5041, which was isolated by us, is an example of the strain used most effectively in the present invention.

Taxonomical properties of the strain K99-5041 are as follows.

1. Morphological Properties

Vegetative mycelia grow well on various agar media and no fragmentation is observed. Aerial mycelia are abundantly grown on yeast-malt extract agar medium and show white to grayish white color. On microscopic observation, chains of more than 20 spores were observed on the aerial mycelia, and the morphological form is flexuous and size of spore is about 0.9–1.1×0.6–0.7 μm with cylindrical form. Surface of the spore is smooth. No sclerotia, sporangia and zoospore are observed.

2. Properties on Various Media

Culture properties of the producing strain of the present invention determined by the method of E. B Shirling and D. Gottlieb (International Journal of Systematic Bacteriology, 16: 313, 1966) are shown in the following.

Color tone was determined referring to Color Harmony Manual, 4th Ed. (Container Corporation of America, Chicago, 1958) as a standard color, and color name as well as attached code number in the parenthesis.

Unless otherwise noted, results are observation of cultures at 27° C. for 2 weeks on various media.

Sucrose-nitrate agar medium

| | |
|---|---|
| Growth | moderate growth, ivory (2db) |
| Reverse side | ivory (2db) |
| Aerial mycelium | poor, alabaster tint (13ba) |
| Soluble pigment | none |

Glucose-asparagine agar medium

| | |
|---|---|
| Growth | poor growth, light ivory (2ca) |
| Reverse side | light ivory (2ca) |
| Aerial mycelium | none |
| Soluble pigment | none |

Glycerol-asparagine agar medium (ISP)

| | |
|---|---|
| Growth | moderate growth, light wheat (2ea) - clove brown (3ni) |
| Reverse side | colonial yellow (2ga) -mustard brown (2ni) |
| Aerial mycelium | none |
| Soluble pigment | slight production, yellow |

Starch-inorganic salt agar medium (ISP)

| | |
|---|---|
| Growth | moderate growth, honey gold (2ic) |
| Reverse side | bamboo (2gc) |
| Aerial mycelium | moderate, alabaster tint (13ba) |
| Soluble pigment | none |

Tyrosine agar medium (ISP)

| | |
|---|---|
| Growth | moderate growth, light tan (3gc) -chestnut brown (4ni) |
| Reverse side | bamboo (2fb) - beaver (3li) |
| Aerial mycelium | none |
| Soluble pigment | slight production, yellow |

Oatmeal agar medium (ISP)

| | |
|---|---|
| Growth | good growth, honey gold (2ic) |
| Reverse side | honey gold (2ic) |
| Aerial mycelium | poor growth, orchid haze (10dc) |
| Soluble pigment | none |

Yeast-malt extract agar medium (ISP)

| | |
|---|---|
| Growth | good growth, light wheat (2ea) |
| Reverse side | honey gold (2ic) |
| Aerial mycelium | abundant growth, dusk (10fe) |
| Soluble pigment | slight production, yellow |

Nutrient agar medium

| | |
|---|---|
| Growth | moderate growth, honey gold (2ic) |
| Reverse side | bamboo (2gc) |
| Aerial mycelium | poor, alabaster tint (13ba) |
| Soluble pigment | none |

Peptone-yeast-iron agar medium (ISP)

| | |
|---|---|
| Growth | moderate growth, light wheat (2ea) |
| Reverse side | bamboo (2gc) |
| Aerial mycelium | none |
| Soluble pigment | slight production, yellow |

Glucose-nitrate agar medium

| | |
|---|---|
| Growth | none |
| Reverse side | none |
| Aerial mycelium | none |
| Soluble pigment | none |

Glycerol-calcium malate agar medium

| | |
|---|---|
| Growth | poor growth, yellow maple (3ng) |
| Reverse side | cinnamon (3le) |
| Aerial mycelium | none |

Glucose-peptone agar medium

| | |
|---|---|
| Growth | moderate growth, honey gold (2ic) |
| Reverse side | mustard gold (2ne) |

-continued

| | |
|---|---|
| Aerial mycelium | slight, white (a) |
| Soluble pigment | none |

3. Physiological Properties
    (1) Formation of melanin pigment
        (a) Tyrosine agar negative
        (b) Peptone-yeast-iron agar medium negative
        (c) Tryptone-yeast liquid negative
        (d) Simple gelatin medium (21–23° C.) negative
    (2) Nitrate reduction negative
    (3) Liquefaction of gelatin (21–23° C.) (simple gelatin medium) negative
    (4) Starch hydrolysis negative
    (5) Coagulation of defatted milk (27° C.) negative
    (6) Peptonization of defatted milk (27° C.) negative
    (7) Growth temperature 12–33° C.
    (8) Utilization of carbon sources (Pridham-Gottlieb agar medium)
        Utilize: D-glucose, myo-inositol
        Slightly utilize: D-fructose
        Not utilize: L-arabinose, D-xylose, D-mannitol, raffinose L-rhamnose, sucrose, melibiose
    (9) Decomposition of cellulose negative
4. Composition of Cell Wall
    2,6-diaminopimelic acid of cell wall is LL type. Main menaquinones are MK-9 ($H_6$) and MK-9 ($H_8$).
5. Conclusion Taxonomical properties of the strain of the present invention are summarized as follows. 2,6-Diaminopimelic acid in the cell wall is LL type and main menaquinones are MK-9 ($H_6$) and MK-9 ($H_8$). Morphology of the spore chain is flexuous, forming with long spore chains and smooth spore surface. Various properties on the culture are exhibiting pale yellow color tone with white to grayish aerial mycelia. No production of melanin pigment is observed, but yellow soluble pigments formation was observed.

The present strain exhibiting the above morphological properties, culture properties and physiological properties was identified as the strain belonging to genus Streptomyces, and was thought to be the strain belonging to the gray series in the classification by Pridham and Tresner (Bergey's Manual of Determinative Bacteriology, 8th Ed., page 748–829, 1974). The strain was deposited as Streptomyces sp. K99-5041 in International Patent Organism Depositary, National Institute of Advanced Industrial Science and Technology, AIST Tsukuba Central 6, 1-1, Higashi 1-chome, Tsukuba-shi, Ibaraki-ken, 305-8566 Japan on Mar. 14, 2002 as permanent depository number FERM P-18765. Thereafter, request for transfer of the strain to the international depositary was accepted on Jan. 9, 2003, under the Budapest Treaty relating to international approval for deposition of microorganisms on the patent procedure in the International Patent Organism Depositary, National Institute of Advanced Industrial Science and Technology, AIST Tsukuba Central 6, 1-1, Higashi 1-chome, Tsukuba-shi, Ibaraki-ken, 305-8566 Japan. The permanent depository number is FERM BP-8272.

K99-5041 substance producing strain as the preferable strain used in the present invention is explained. However, since the morphological properties of microorganisms are generally very easily mutated and are not constant. Natural mutation or artificial mutation generally performed by ultraviolet irradiation or chemical mutagens such as N-methyl-N'-nitro-N-nitrosoguanidine and ethyl methansulfonate, are well known. The strain belonging to genus Streptomyces and having ability to produce K99-5041 substance, including the artificial mutants as well as natural mutants, can be used in the present invention. In addition, all strains belonging to genus Streptomyces and having ability to produce K99-5041 substance including strains mutated by cell engineering technology such as cell fusion, gene manipulation, etc., can be used in the present invention.

In production of K99-5041-C1x substance and/or K99-5041-C2x substance of the present invention, at first, K99-5041 substance producing strain belonging to genus Streptomyces is cultured in a preferable medium. In the culture of the strain, conventional medium for culturing fungi was generally applied. Medium containing assimilable carbon sources for microorganism, digestible nitrogen sources and, if necessary, inorganic salts can be used as nutrient medium.

Examples of assimilable carbon sources are glucose, sucrose, molasses, starch, dextrin, cellulose, glycerin, organic acid, etc. are used independent or in combination. Examples of digestible nitrogen sources are organic nitrogen sources such as peptone, meat extract, yeast extract, dry yeast, soybean powder, corn steep liquor, cotton seed powder, casein, soybean protein hydrolyzate, amino acids and urea, and inorganic nitrogen sources such as nitrates and ammonium salts are used independent or in combination.

If necessary, inorganic salts or heavy metallic salts such as sodium, potassium, calcium, magnesium, phosphate, etc. are added. Further, if necessary, trace nutrients, growth promoting agents and precursors preferable for production of K99-5041 substance are optionally added.

Culture is preferably performed by aerobic condition such as conventional shake culture or aeration agitation culture. For industrial culture, submerged aeration agitating culture is preferable. The pH of the medium is preferably performed at neutral condition. Culturing temperature can be performed at 20–37° C., generally at 24–30° C., preferably at 27° C. In case of liquid culture, when culture is performed generally for 3–6 days, K99-5041 substance of the present invention is produced and accumulated, and when the amount of accumulation reaches maximum in the culture medium, the cultivation may preferably be terminated.

A condition of culture such as composition of culture, properties of liquid culture medium, culturing temperature, agitation rate and amount of aeration may naturally be adjusted and selected in order to obtain preferable result of cultivation depending on types of strain and external condition. In the liquid culture, if foaming occurs, antifoam agents such as silicone oil, vegetable oil and surface active agent can preferably be used.

Since K99-5041 substance accumulated in the thus obtained cultured broth is contained in the cultured filtrate or cultured mycelia, the cultured broth is filtered with optionally adding filter aid such as Celite, Hyflosupercell, etc., or is centrifuged to separate into the cultured filtrate and the mycelia, then organic solvent extracts from the cultured filtrate and mycelia are concentrated and K99-5041 substance is preferably collected therefrom.

Isolation of K99-5041 substance from the cultured filtrate can be performed by extracting the cultured filtrate with water immiscible organic solvent such as ethyl acetate, butyl acetate and benzene, and concentrating the extract in vacuo to obtain crude K99-5041 substance. The crude substance is treated by conventional known method used for purification of fat-soluble substances, for example, column chromatography using carrier such as silica gel and alumina to isolate and purify K99-5041 substance.

In order to isolate K99-5041 substance from mycelia, the mycelia are extracted by aqueous water miscible organic solvent such as acetone and aqueous methanol. The obtained extract is concentrated in vacuo, and the concentrated material is extracted with water immiscible organic solvent such as ethyl acetate, butyl acetate and benzene, then the thus obtained extract is combined with the extract obtained from the above culture liquid and is treated for separation and purification of K99-5041 substance. Further, K99-5041 substance can be isolated and purified by the same method described hereinabove.

Physicochemical properties of K99-5041-C1x substance and K99-5041-C2x substance of the present invention are described as follows.

[I] K99-5041-C1x substance
(1) Molecular formula: $C_{22}H_{41}N$ [High resolution FAB mass spectrometry: m/z 319.3234 (M)] (Calculated: 319.3239)
(2) Molecular weight: 319 [EI mass spectrometry: m/z 319 (M)$^+$]
(3) Specific rotation: $[\alpha]_D^{24}=-3.2°$ (c=0.26, methanol)
(4) Ultraviolet absorption spectrum (in methanol): as shown in FIG. 1, maximum absorption at 235 nm (log ε=14,500)
(5) Infrared absorption spectrum (KBr Tablet): as shown in FIG. 2, $\lambda max^{KBr}$ cm$^{-1}$: 3435, 2924, 2854, 1606, 1466, 1385
(6) Solubility in solvent: soluble in methanol, ethanol, acetonitrile, ethyl acetate, chloroform and dimethyl sulfoxide, and insoluble in water.
(7) Grouping for acidic, neutral and basic: Weak basic substance.
(8) Color and form of substance: pale yellow oily substance.
(9) Proton nuclear magnetic resonance spectrum: Proton nuclear magnetic resonance spectrum measured by using JEOL, nuclear magnetic resonance spectrometer (in deuteriochloroform, 500 MHz) is as shown in FIG. 3. Chemical shifts (ppm) are as follows. 0.86 (6H), 1.15 (2H), 1.2–1.4 (20H), 1.43 (2H), 1.51 (1H), 2.06 (3H), 2.10 (2H), 2.48 (2H), 3.86 (2H), 5.75 (1H).
(10) Carbon nuclear magnetic resonance spectrum: Carbon nuclear magnetic resonance spectrum measured by using JEOL, nuclear magnetic resonance spectrometer (in deuteriochloroform, 125.65 MHz) is as shown in FIG. 4. Chemical shifts (ppm) are as follows. 15.9 (1C), 22.7 (2C), 26.8 (1C), 27.4 (1C), 28.0 (1C), 29.0 (1C), 29.4–30.0 (9C), 30.5 (1C), 39.1 (1C), 57.8 (1C), 126.3 (1C), 143.2 (1C), 171.7 (1C).

As described hereinabove, as the results of examining various physicochemical properties and spectral data of K99-5041-C1x substance, K99-5041-C1x substance was determined as having chemical structure represented by the following formula [I].

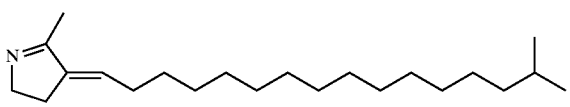

[I]

[II] K99-5041-C2x substance
(1) Molecular formula: $C_{22}H_{41}N$ [High resolution FAB mass spectrometry: m/z 319.3224 (M$^+$)] (Calculated: 319.3239)
(2) Molecular weight: 319 [EI mass spectrometry: m/z 319 (M)$^+$]
(3) Specific rotation: $[\alpha]_D^{24}=-1.2°$ (c=0.17, methanol)
(4) Ultraviolet absorption spectrum (in methanol): as shown in FIG. 5, maximum absorption at 235 nm (log ε=13,900)
(5) Infrared absorption spectrum (KBr Tablet): as shown in FIG. 6, $\lambda max^{KBr}$ cm$^{-1}$: 3431, 2924, 2852, 1606, 1466, 1385, 1261, 1099, 1032, 804.
(6) Solubility in solvent: soluble in methanol, ethanol, acetonitrile, ethyl acetate, chloroform and dimethyl sulfoxide, and insoluble in water.
(7) Grouping for acidic, neutral and basic: Weak basic substance.
(8) Color and form of substance: white oily substance.
(9) Proton nuclear magnetic resonance spectrum: Proton nuclear magnetic resonance spectrum measured by using JEOL, nuclear magnetic resonance spectrometer (in deuteriochloroform, 500 MHz) is as shown in FIG. 7. Chemical shifts (ppm) are as follows. 0.88 (3H), 1.2–1.4 (26H), 1.43 (2H), 2.06 (3H), 2.10 (2H), 2.48 (2H), 3.86 (2H), 5.75 (1H).
(10) Carbon nuclear magnetic resonance spectrum: Carbon nuclear magnetic resonance spectrum measured by using JEOL, nuclear magnetic resonance spectrometer (in deuteriochloroform, 125.65 MHz) is as shown in FIG. 8. Chemical shifts (ppm) are as follows. 14.1 (1C), 15.9 (1C), 22.7 (1C), 26.8 (1C), 29.0 (1C), 29.4–29.7 (11C), 30.5 (1C), 31.9 (1C), 57.8 (1C), 126.2 (1C), 143.2 (1C), 171.7 (1C).

As described hereinabove, as the results of examining various physicochemical properties and spectral data of K99-5041-C2x substance, K99-5041-C2x substance was determined as having chemical structure represented by the following formula [II]

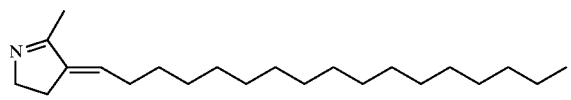

[II]

Various physicochemical properties of K99-5041-C1x substance and K99-5041-C2x substance were described hereinabove in detail. Compounds having identical properties have not been reported, and K99-5041-C1x substance and K99-5041-C2x substance are determined as novel substances.

Biological properties of K99-5041 substance of the present invention are described hereinbelow.
(1) Inhibitory Action Against Lanosterol Synthase of Human Origin Lanosterol synthase activity was assayed by partially modified method of Kusano et al (Chem. Pharm. Bull. 39, 239–241, 1991). Enzyme origin used is as follows. Lanosterol synthase cDNA derived from human origin (Sung et al. Biol. Pharm. Bull., 18, 1459–1461, 1995) was expressed by glyceraldehydes-3-phosphate dehydrogenase promoter in lanosterol synthase deficient yeast GIL77 (Kushiro et al., Eur. J. Biochem., 256, 238–241, 1998). The thus obtained cell-free extract derived from transformed yeast was used.

The above transformed yeast was homogenized in buffer A [0.1 M potassium-phosphate buffer solution (pH 7.4), 0.45 M sucrose, 1 mM EDTA and 1 mM dithiothreitol] in the presence of acid treated glass beads using Waring blender

[Type 500ACD, Sakuma Seisakusho Co., Japan]. Supernatant obtained by centrifugation, 8600×g, was prepared to make protein concentration of 10 mg/ml by adding the buffer A hereinabove to prepare the cell-free extract.

A substrate, [$^{14}$C](3S)-2,3-oxidosqualene was prepared biosynthetically by culturing lanosterol deficient yeast GL7 (Gollub et al. J. Biol. Chem. 252, 2846–2854, 1977) in the presence of [1-$^{14}$C]sodium acetate to incorporate the radioactivity into oxidosqualene.

Assay of lanosterol synthase was performed as follows. [$^{14}$C](3S)-2,3-oxidosqualene (final concentration, 0.17–0.42 $\mu$M, 4.5 nCi) and K99-5041 substance were added in buffer B [0.1 M potassium-phosphate buffer (pH 7.4) and 0.1% Triton X-100] to prepare total volume 900 $\mu$l, preincubated at 37° C. for 10 minutes, added enzyme 1 mg protein to prepare total 1 ml, and incubated at 37° C. for 60 minutes.

Subsequently, 6% potassium hydroxide/ethanol was added thereto to terminate the reaction, and the mixture was saponificated by incubating at 37° C. for 10 minutes, added cyclohexane 2 ml and stirred well. The cyclohexane layer 1.6 ml was dried up, spotted on TLC plate [silica gel plate (with concentration zone), Merck Inc., U.S.A., thickness 0.25 mm: Art. No. 11798] and developed with solvent of benzene/acetone (19:1, v/v). Next, amounts of unreacted [$^{14}$C](3S)-2,3-oxidosqualene and generated [$^{14}$C]lanosterol were quantitatively assayed using the photo image analyzer BAS-1500 (Fuji Photo Film Co., Japan) to calculate inhibition rate of lanosterol synthesis.

As the results, 50% inhibition concentration ($IC_{50}$) for lanosterol synthase activity of K99-5041 substance was determined as 15 $\mu$M for K99-5041-C1x substance and 18 $\mu$M for K99-5041-C2x substance.

As explained in detail, since K99-5041 substance of the present invention exhibits inhibitory action against lanosterol synthase, it is expected to be useful for preventive and therapeutic agents for disease caused by cholesterol accumulation in humans and antifungal agents.

BEST MODE FOR CARRYING OUT THE INVENTION

Figure 1:
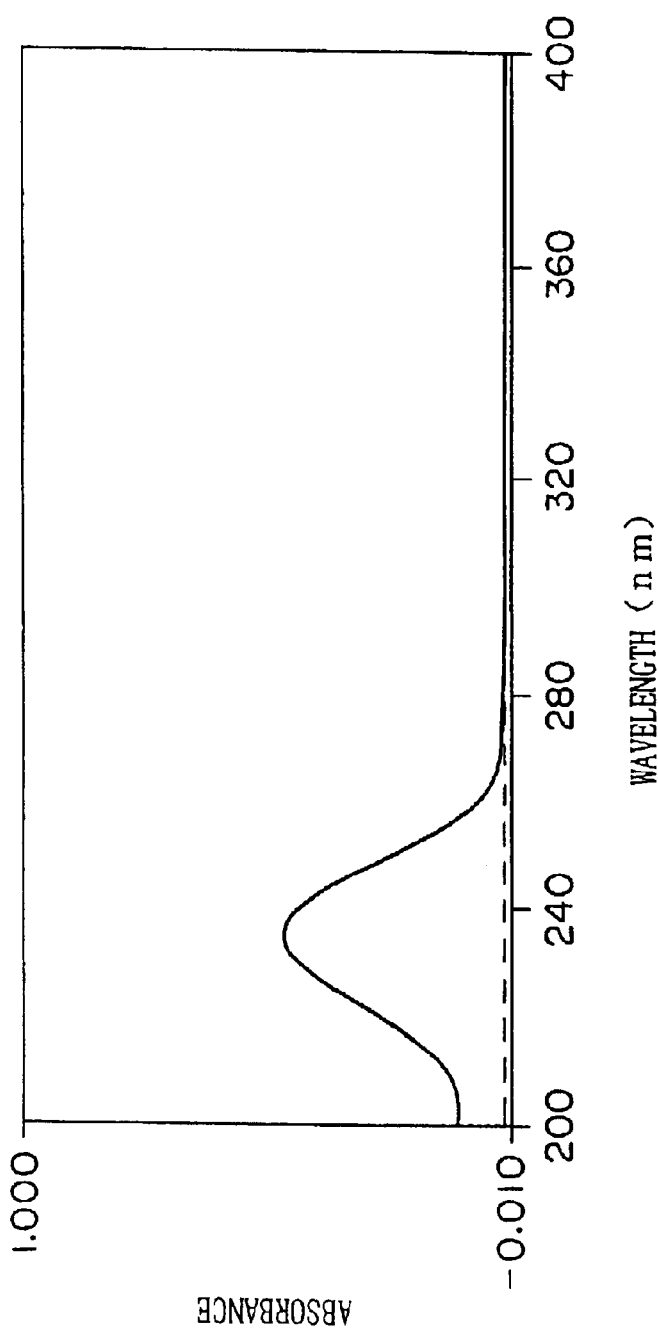
FIG. 1 shows ultraviolet absorption spectrum (in $CH_3OH$) of K99-5041-C1x substance of the present invention.
Figure 2:
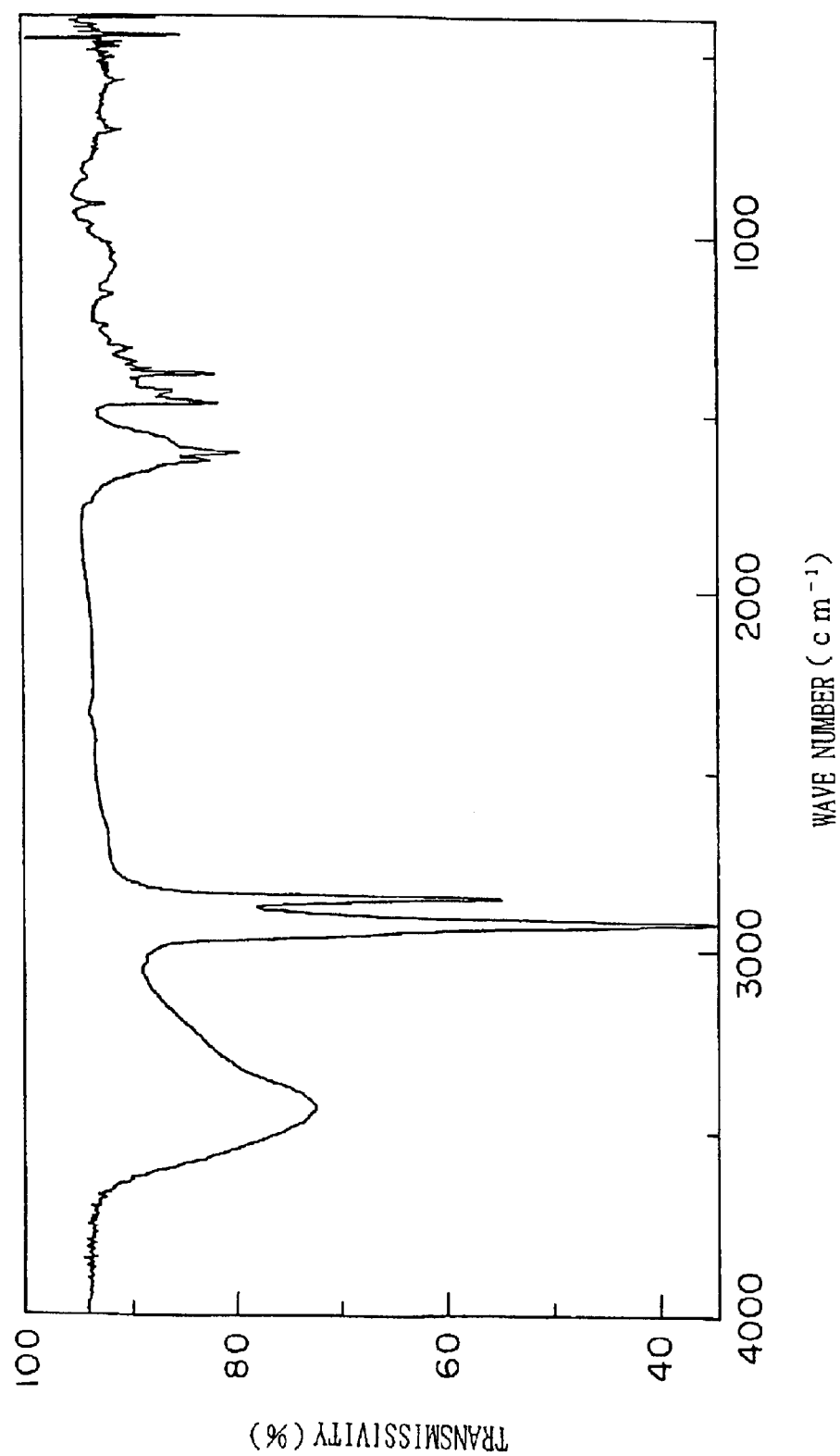
FIG. 2 shows Infrared absorption spectrum (KBr tablet) of K99-5041-C1x substance of the present invention.
Figure 3:
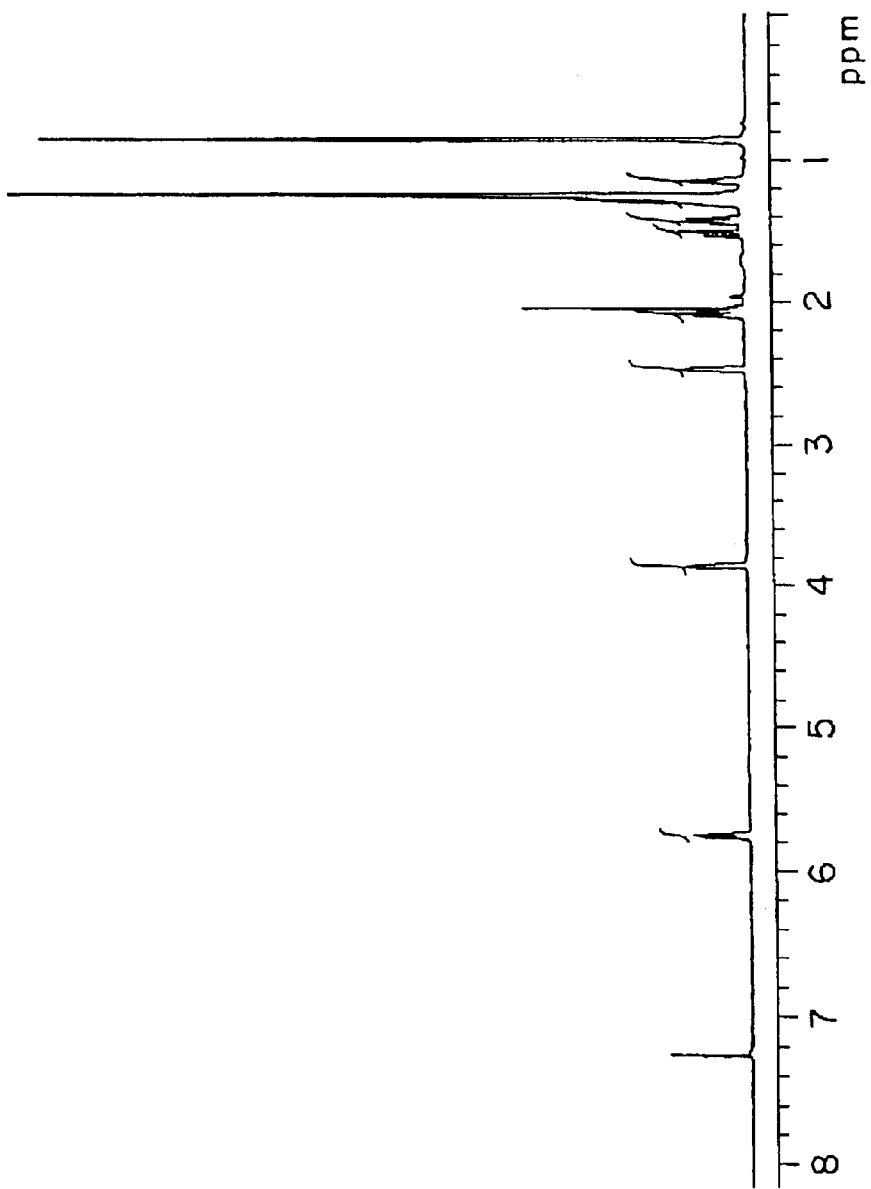
FIG. 3 shows proton nuclear magnetic resonance spectrum (in $CDCl_3$) of K99-5041-C1x substance of the present invention.
Figure 4:
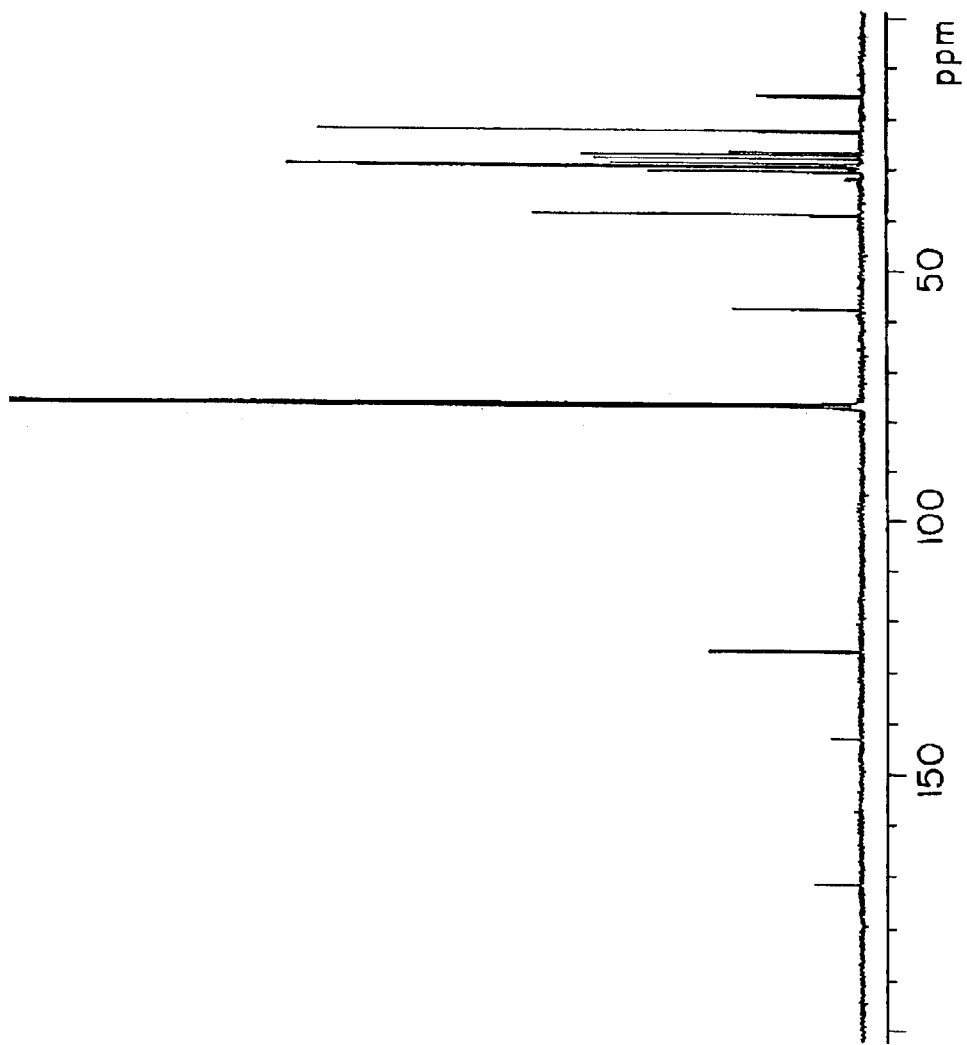
FIG. 4 shows carbon nuclear magnetic resonance spectrum (in $CDCl_3$) of K99-5041-C1x substance of the present invention.
Figure 5:
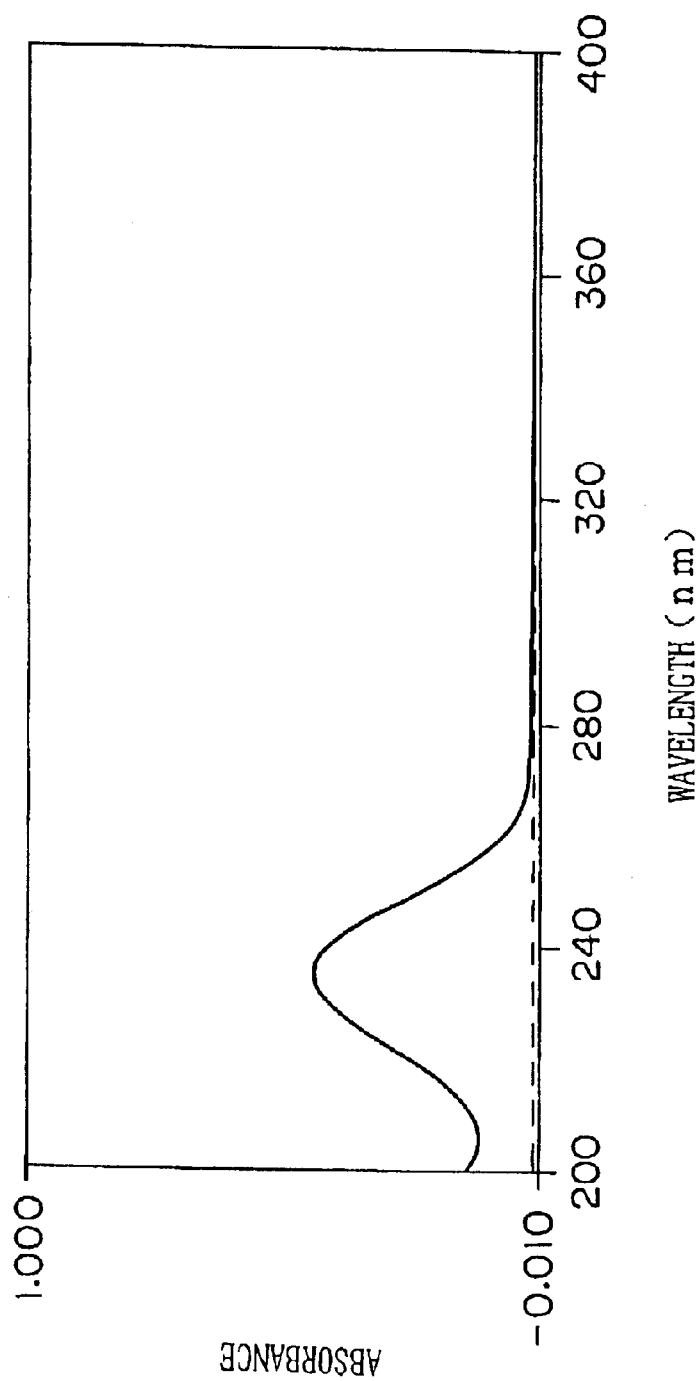
FIG. 5 shows ultraviolet absorption spectrum (in $CH_3OH$) of K99-5041-C2x substance of the present invention.
Figure 6:
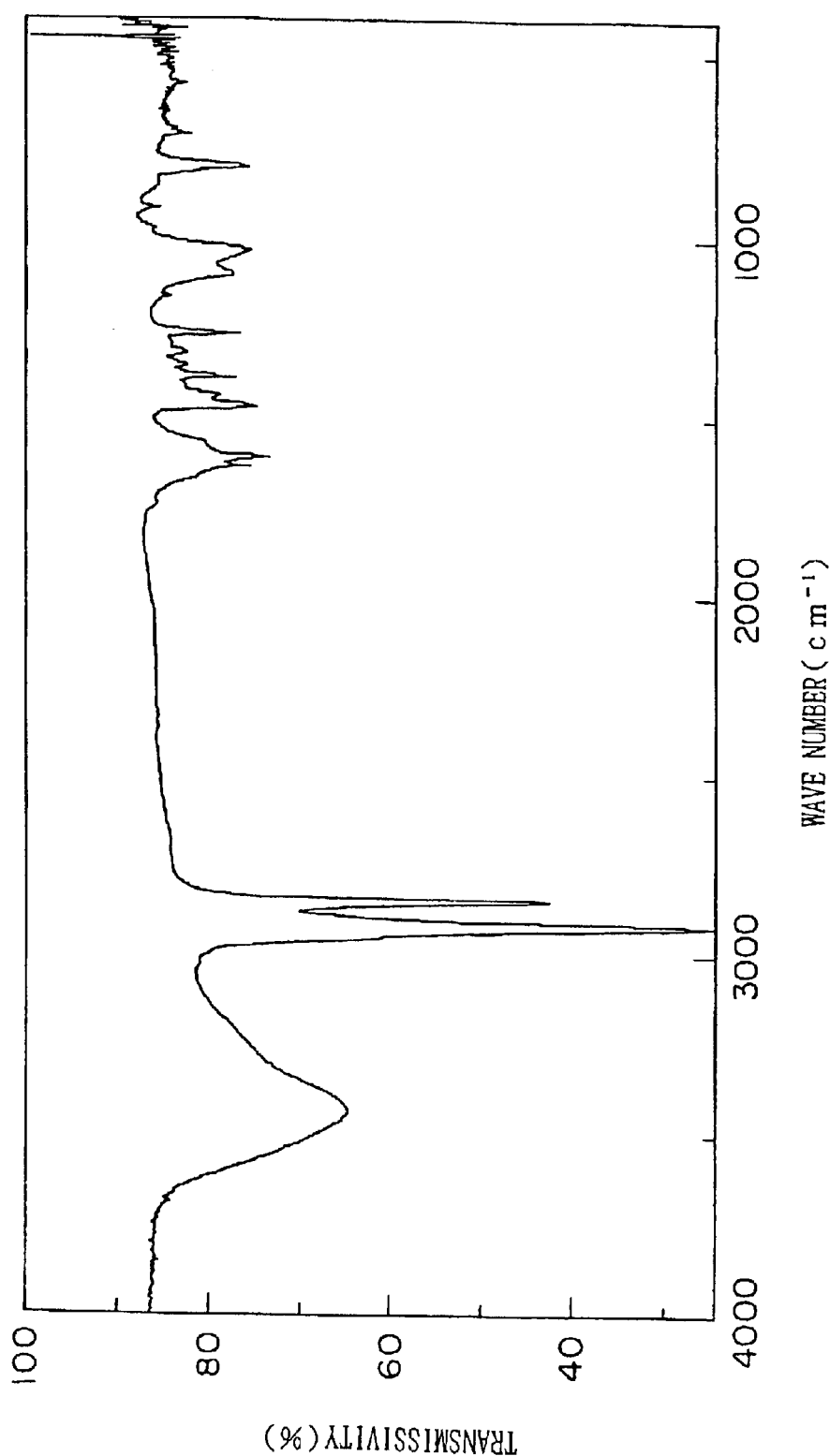
FIG. 6 shows Infrared absorption spectrum (KBr tablet) of K99-5041-C2x substance of the present invention.
Figure 7:
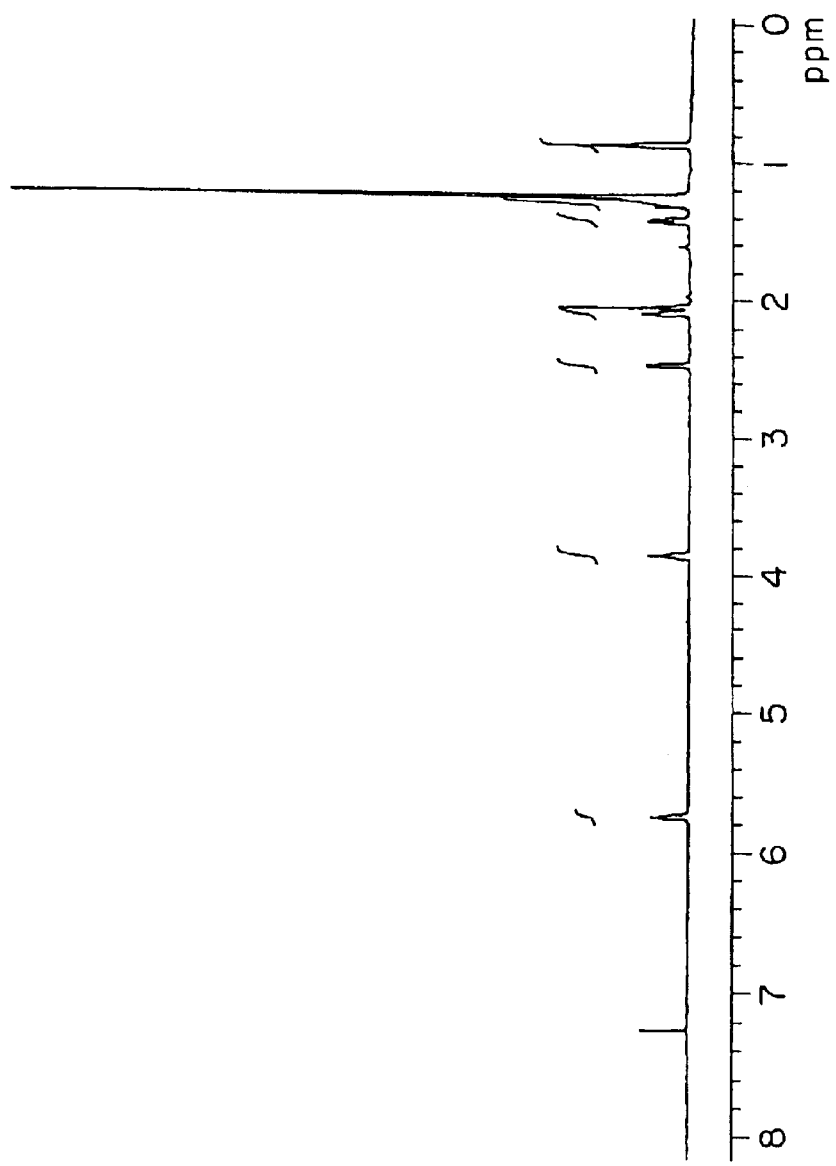
FIG. 7 shows proton nuclear magnetic resonance spectrum (in $CDCl_3$) of K99-5041-C2x substance of the present invention.
Figure 8:
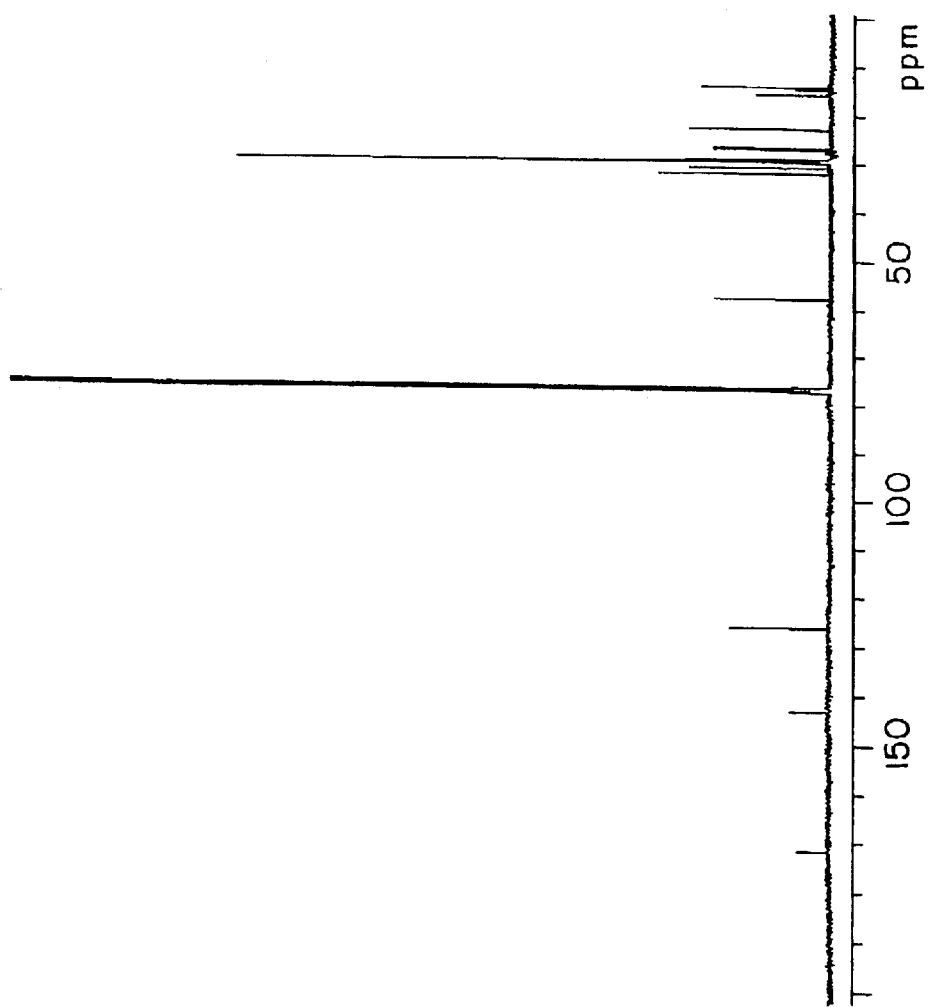
FIG. 8 shows carbon nuclear magnetic resonance spectrum (in $CDCl_3$) of K99-5041-C2x substance of the present invention.

The present invention is explained by mentioning example, but is not limited within the example.

A medium 100 ml (adjusted to pH 7.0) containing starch 2.4%, yeast extract 0.5%, glucose 0.1%, peptone 0.3%, meat extract 0.3% and $CaCO_3$ 0.4% was poured into a 500 ml Erlenmeyer flask, sealed with cotton plug and steam sterilized. Spores of Streptomyces sp. K99-5041 grown on the agar medium were aseptically inoculated thereto and shake cultured at 27° C. for 3 days to obtain a seed culture liquid.

A medium 20 lit. containing glucose 0.5%, corn steep liquor 1.0%, oat meal 1.0%, Pharmamedia 1.0%, $K_2HPO_4$ 0.1%, $MgSO_4 \cdot 7H_2O$ 0.1% and metal solution 1 ml/lit. ($FeSO_4 \cdot 7H_2O$, $MnCl_2 \cdot 4H_2O$, $ZnSO_4 \cdot 7H_2O$, $CuSO_4 \cdot 5H_2O$ and $CoCl_2 \cdot 6H_2O$, each 1 g, dissolved in water 1 lit.) was poured into 30 lit. jar-fermenter and steam sterilized. The above seed culture liquid 200 ml was aseptically inoculated thereto.

After the medium was cultured at 27° C. for 6 days with aeration, cultured broth 20 lit. was treated with ethyl acetate 18 lit. The mixture was centrifuged at 12,000 rpm using Kokusan Type S ultracentrifuge to separate organic layer and inorganic layer. The organic layer was concentrated in vacuo to obtain crude substance 15.7 g. Part of the substance (5.5 g) was charged on a column of silica gel [500 g, Wako gel (registered trade mark) C-200, Wako Pure Chemicals Co., Japan] and eluted stepwisely with chloroform 0.4 lit., chloroform-methanol (50:1) 1.5 lit. and chloroform-methanol (35:1) 1.0 lit., in this order.

Chloroform-methanol (35:1) fraction containing K99-5041-C1x component and K99-5041-C2x component was collected and dried in vacuo to obtain red-brownish crude substance 124 mg. The methanol soluble fraction thereof was charged on a cartridge for sample pretreatment (TOYOPAK ODS-M, Toso Corp., Japan) to obtain non-adsorbed fraction 104 mg.

A sample 97 mg thereof was charged on high performance liquid chromatography [HPLC. Equipment: CCPM, Toso Corp., Japan, Column: Lobar column size B LiChroprep RP-18 (size: 25×310 mm, particle size: 40–63 $\mu$m, Art. No. 10625), Detection: UV 234 nm, Flow rate: 4 ml/min., Elution: 98% methanol-water for 250 min. and thereafter 100% methanol for 400 min.] and collected fractions as follows: one fraction from elution time 100 minutes to 150 minutes; six fractions from elution time 150 minutes to 300 minutes in each 25 minutes intervals; and one fraction from 300 minutes to 400 minutes, in total 8 fractions. Each fraction was concentrated in vacuo to prepare aqueous methanol solution of about 3 ml.

Three fractions collected from 175 minutes to 200 minutes, 200 minutes to 225 minutes, and 225 minutes to 250 minutes, respectively, were independently purified using HPLC [Equipment: CCPE-II, Toso Corp., Japan, Column: TSK gel ODS-80T$_M$ (size: 8×300 mm, particle size: 5 $\mu$m), Detection: UV 234 nm, Flow rate: 2 ml/min., Elution: 98% methanol-water, Charging: 150–450 $\mu$l/one injection]. Purification was repeated until single peak was given to obtain a fraction at elution time 29 minutes (designates as C1) 4.2 mg and a fraction at elution time 31 minutes (designates as C2) 2.6 mg.

C1 and C2 were dissolved in methanol 1 ml, respectively. These were independently purified repeatedly using HPLC [Equipment: Model 8020, Toso Corp., Japan, Column: TSK gel ODS-120T (size: 4.6×150 mm, particle size: 5 $\mu$m), Detection: UV 234 nm, Flow rate: 1.5 ml/min., Elution: 100% methanol, Charging: 50–250 $\mu$l/one injection].

Under the condition hereinabove, in any of C1 and C2, crude substances, which are estimated as analogues having a cis-double bond in the side chain for elution time 8 minutes, were eluted and peaks eluting thereafter were shown tailing for long time. Consequently, each fraction of retention time after 8 minutes was collected for 30–40 minutes or more, then K99-5041-C1x substance 3.5 mg was obtained from C1 and K99-5041-C2x substance 3.5 mg was obtained from C2.

INDUSTRIAL APPLICABILITY

A microorganism belonging to genus Streptomyces and having ability to produce K99-5041-C1x substance and K99-5041-C2x substance is cultured in a medium, and K99-5041-C1x substance and K99-5041-C2x substance are collected from the cultured broth. Substances having inhibitory activity against lanosterol synthase are obtained. The substances are expected on effects for prevention and treatment of adult diseases such as myocardial infarction and cerebral apoplexy caused by hyperlipidemia and arteriosclerosis, and as antifungal agents.

What is claimed is:

1. K99-5041-C1x substance represented by the following Formula [I]:

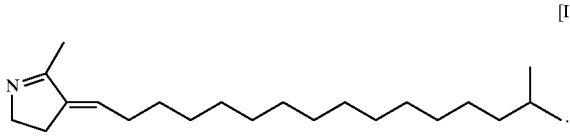

2. K99-5041-C2x substance represented by the following formula [II]:

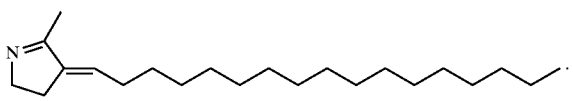

3. A medicament of K99-5041 substance comprising K99-5041-C1x substance represented by the following formula [I]:

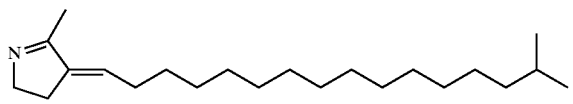

and K99-5041-C2x substance represented by the following formula [II]:

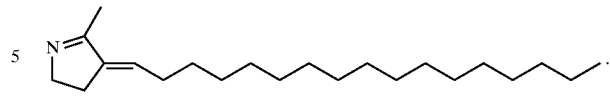

4. A medicament comprising the compound of claim 1.
5. A medicament comprising the compound of claim 2.
6. A medicament comprising K99-5041-C1x substance represented by the following formula [I]:

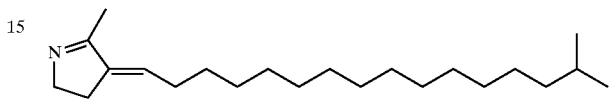

or K99-5041-C2x substance represented by the following formula [[II]]

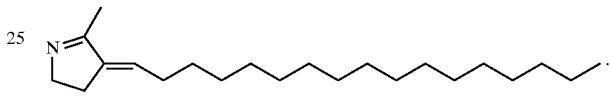

7. A method of inhibiting lanosterol synthase which comprises administering the compound of claim 1 to 2,3-oxidosqualene.
8. A method of inhibiting lanosterol synthase which comprises administering the compound of claim 2 to 2,3-oxidosqualene.
9. A method of inhibiting lanosterol synthase which comprises administering the composition of claim 3 to 2,3-oxidosqualene.
10. A method of treating myocardial infarction or cerebral apoplexy based on hyperlipidemia and arteriosclerosis caused by accumulation of cholesterol in humans, which comprises administering an effective amount of the compound of claim 1.
11. A method of treating myocardial infarction or cerebral apoplexy based on hyperlipidemia and arteriosclerosis caused by accumulation of cholesterol in humans, which comprises administering an effective amount of the compound of claim 2.
12. A method of treating myocardial infarction or cerebral apoplexy based on hyperlipidemia and arteriosclerosis caused by accumulation of cholesterol in humans, which comprises administering an effective amount of the composition of claim 3.

* * * * *